(12) United States Patent
Yarita

(10) Patent No.: US 6,201,981 B1
(45) Date of Patent: Mar. 13, 2001

(54) ELECTRODE FOR MEASURING BIOMEDICAL SIGNAL AND ELECTRODE SUPPORT DEVICE FOR MEASURING A BIOMEDICAL SIGNAL

(75) Inventor: Masaru Yarita, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 0 days.

(21) Appl. No.: 09/090,409

(22) Filed: Jun. 4, 1998

(30) Foreign Application Priority Data

Jun. 4, 1997 (JP) .................................................. 9-146278

(51) Int. Cl.$^7$ ...................................................... A61B 5/04
(52) U.S. Cl. .......................... 600/372; 600/393; 600/411; 128/901
(58) Field of Search ..................................... 600/377, 382, 600/372, 388, 389, 393, 395, 409, 411; 607/152; 128/901

(56) References Cited

U.S. PATENT DOCUMENTS

| | | | |
|---|---|---|---|
| 4,233,987 | * 11/1980 | Feingold | 600/382 |
| 4,328,814 | * 5/1982 | Arkans | 600/393 |
| 4,852,572 | * 8/1989 | Nakahashi et al. | 128/640 |
| 5,038,785 | * 8/1991 | Blakeley et al. | 128/653.2 |
| 5,178,145 | * 1/1993 | Rea . | |
| 5,370,116 | * 12/1994 | Rollman et al. | 600/393 |
| 5,436,564 | * 7/1995 | Kreger et al. | 128/696 |
| 5,697,958 | * 12/1997 | Paul et al. | 607/31 |
| 5,855,552 | * 1/1999 | Houser et al. | 600/374 |

FOREIGN PATENT DOCUMENTS 39-6183   5/1939   (JP) ........................................ 94/153

OTHER PUBLICATIONS

Wolf et al. "Student Reference Manual for Electronic Instrumentation Laboratories", Prentice Hall Pub. 1990.*
Catalog For An Electrode Located In The Cranium, AD–Tech Medical Instrument Corporation; Nihon Kohden; catalog No. 930–850.

* cited by examiner

*Primary Examiner*—Linda C. M. Dvorak
*Assistant Examiner*—David M. Ruddy
(74) *Attorney, Agent, or Firm*—Sughrue, Mion, Zinn, Macpeak & Seas, PLLC

(57) ABSTRACT

An electrode for measuring a biomedical signal has: thin foil electrodes 11*a* to 11*c* which are formed into a square shape; lead wires 12*a* to 12*c* which are connected to the electrodes 11*a* to 11*c*, respectively; and a support section 13 which is made of a flexible material such as rubber or plastic, formed into a slender thin plate-like shape, and supports the electrodes 11*a* to 11*c* in a straight line and at constant intervals. The lead wires 12*a* to 12*c* are twisted.

11 Claims, 7 Drawing Sheets

↑
A

ELECTRODE FOR MEASURING BIOMEDICAL SIGNAL AND ELECTRODE SUPPORT DEVICE FOR MEASURING A BIOMEDICAL SIGNAL

BACKGROUND OF THE INVENTION

1. Field of the Invention

The invention relates to an electrode for measuring a biomedical signal and an electrode support device for measuring a biomedical signal which are preferably used in a medical measuring apparatus for measuring vital information, such as an electroencephalograph or an electrocardiograph.

2. Related art

Conventionally, in MRI (Magnetic Resonance Instrument) diagnosis, an electroencephalogram or an electrocardiogram is measured. FIG. 10 is a view diagrammatically showing the configuration of MRI.

The case where an electroencephalogram or an electrocardiogram is to be obtained in MRI will be considered. In a strong magnetic field formed in MRI magnet of the MRI, a movement of the body of the subject causes a voltage in conformance to Faraday's law of electromagnetic induction to appear in lead wires of electrodes of an electroencephalograph or an electrocardiograph. Such a voltage functions as noises, and produces a problem in that the measurement cannot be correctly performed. This problem is produced also by a minute movement of the body of the subject caused by the heartbeat. Therefore, it is requested to develop a countermeasure to the problem as soon as possible. FIG. 11 shows an electrocardiogram and the waveform of noises. From the figure, it will be seen that noises appear in synchronization with the electrocardiogram. The noise level varies depending on the site to which an electrode is attached and the manner of drawing out a lead wire therefrom, and is in proportion to the number of crossing magnetic fluxes.

SUMMARY OF THE INVENTION

Conventionally, in order to solve this problem, the arrangement direction of lead wires of electrodes is made coincident with the direction of the line of magnetic force so that the opening area with respect to the line of magnetic force is reduced, or a filter is disposed in a signal processing circuit. However, such countermeasures are insufficient for suppressing noises.

Therefore, it is an object of the invention to provide an electrode for measuring a biomedical signal and an electrode support device for measuring a biomedical signal which, when used in a magnetic field, can suppress noises generated in lead wires connected to electrodes of an electroencephalograph or an electrocardiograph, to a low level.

In order to attain the object, according to the present invention, there is provided the electrode for measuring a biomedical signal including a plurality of electrodes for taking out a biomedical signal; lead wires respectively connected to the electrodes; and a support member which supports the electrodes and the lead wires, and which is made of a flexible and insulative material such as plastic or rubber, and the lead wires are tightly twisted in the support member and the twisted lead wires are disposed in a straight line.

According to this configuration, the lead wires respectively connected to the electrodes are tightly twisted in the support member. Consequently, even when the electrode is placed in a magnetic field, there is little opening area with respect to the line of magnetic force. As a result, even when the electrode is used together with an apparatus such as MRI which produces a strong magnetic field, a voltage induced in each lead wire is very low in level, and hence an electrocardiogram or an electroencephalogram can be correctly measured.

The electrode for measuring a biomedical signal of the invention comprises: a plurality of electrodes for taking out a biomedical signal; lead wires respectively connected to the electrodes; and a support member which is made of a flexible and insulative material such as plastic or rubber, and in which the electrodes are stacked so as not to overlap one another and the lead wires are stacked so as to overlap one another in a noncontact state.

According to this configuration, the electrodes are stacked so as not to overlap one another and the lead wires are stacked so as to overlap one another in a noncontact state. Therefore, the opening area of each lead wire with respect to the line of magnetic force is reduced. As a result, even when the electrode is used together with an apparatus such as MRI which produces a strong magnetic field, a voltage induced in each lead wire is very low in level, and hence an electrocardiogram or an electroencephalogram can be correctly measured.

Furthermore, a sensor which, when placed in a magnetic field, generates a current corresponding to the number of crossing magnetic fluxes may be disposed in the support member. For example, the sensor is configured by disposing a conductive wire in the support member, in a shape of a loop.

The electrode support device for measuring a biomedical signal of the invention comprises: a plurality of housing portions which are made of a flexible and insulative material such as plastic, or rubber, and which respectively house a plurality of electrodes for taking out a biomedical signal; and a groove through which lead wires respectively connected to the electrodes are drawn out in a straight line to an outside.

According to this structure, the lead wires can be linearly fixed, and hence the opening area with respect to the line of magnetic force in the stack direction can be reduced. As a result, even when the electrode support device is used together with an apparatus such as MRI which produces a strong magnetic field, a voltage induced in each lead wire is very low in level, and hence an electrocardiogram or an electroencephalogram can be correctly measured.

The electrode support device may further comprise an accommodating portion which accommodates a sensor which generates a current corresponding to the number of crossing magnetic fluxes.

BRIEF DESCRIPTION OF THE DRAWINGS

FIG. 1(*b*) is a plan view showing a modified embodiment of a first Embodiment of the invention;

DETAILED DESCRIPTION OF THE PREFERRED EMBODIMENTS

Hereinafter, embodiments of the electrode for measuring a biomedical signal and the electrode support device for measuring a biomedical signal of the invention will be described with reference to the accompanying drawings.

First Embodiment of the Electrode for Measuring a Biomedical Signal

Figure 1A:
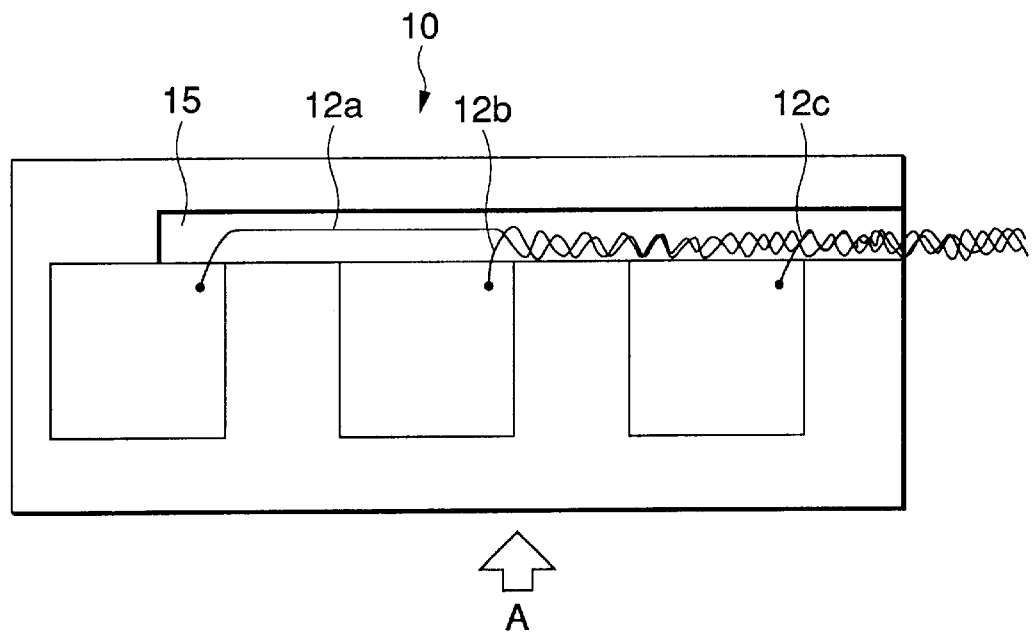
FIG. 1(*a*) is a plan view showing a first Embodiment of the electrode for measuring a biomedical signal of the invention.
Figure 1B:
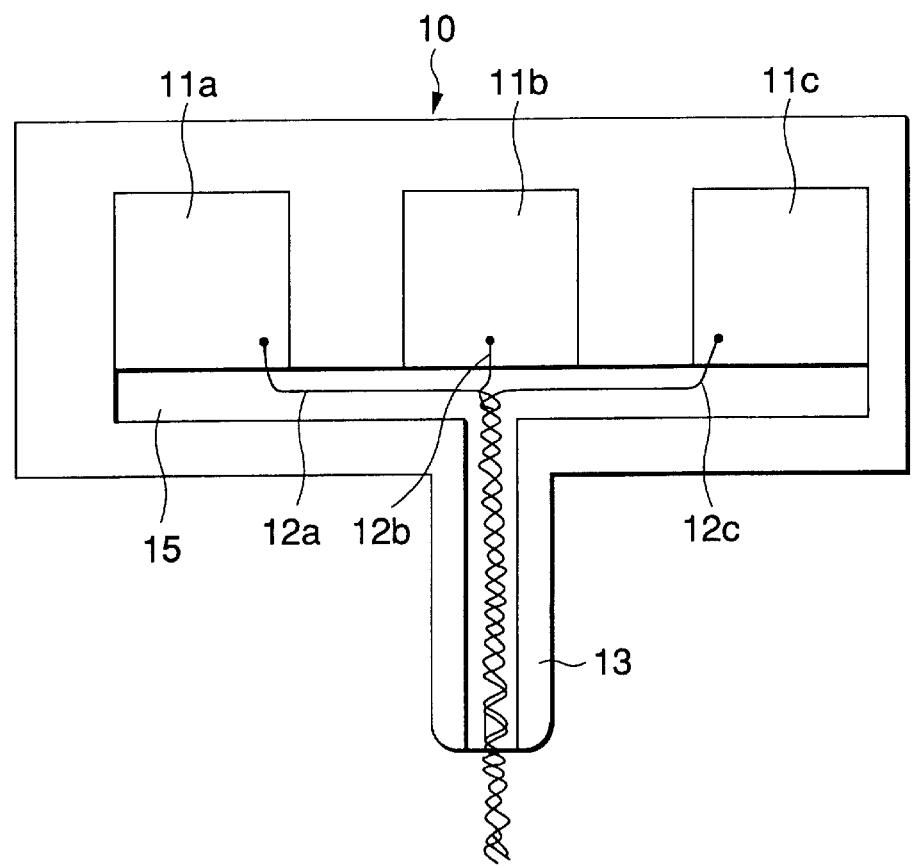
Figure 2:
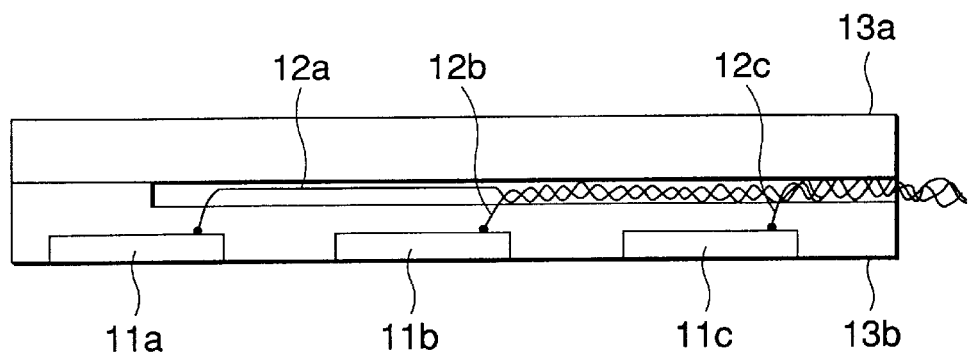
FIG. 2 is a section view taken along the line A—A of FIG. 1.

FIG. 1 is a perspective view from the upper side showing a first Embodiment of the electrode for measuring a biomedical signal of the invention, and FIG. 2 is a section perspective view from the arrow A of FIG. 1.

The electrode for measuring a biomedical signal 10 of the first embodiment includes thin foil electrodes 11a to 11c which are formed into a square shape; lead wires 12a to 12c which are connected to the electrodes 11a to 11c, respectively; and a support section 13 which is made of a flexible material such as rubber or plastic, formed into a slender thin plate-like shape, and supports the electrodes 11a to 11c in a straight line and at constant intervals.

The electrodes 11a and 11c are used for taking out a biomedical signal. One of the electrodes is a positive electrode (+) and the other electrode is a negative electrode (−). The electrode 11b is a reference electrode (E). The lead wires 12a to 12c are tightly twisted so as not to have an opening area with respect to the line of magnetic force. As shown in the section view of FIG. 2, the support section 13 consists of two plate-like members 13a and 13b which are bonded to each other by an adhesive agent. A groove 15 (see FIG. 1) which is very thin and through which the lead wires 12a to 12c are to be passed is formed in the plate-like member 13a so as to elongate in the longitudinal direction. The lead wires 12a to 12c in a twisted state are inserted into the groove 15. An insulation cover is formed on each of the lead wires 12a to 12c, so that the lead wires are not short-circuited as a result of the twisting. Also the portions of the lead wires 12a to 12c which are drawn out to the outside from the support section 13 are tightly twisted so as to have a reduced opening area with respect to the line of magnetic force.

Since the electrode for measuring a biomedical signal 10 is configured as described above and the lead wires 12a to 12c connected to the electrodes 11a to 11c are tightly twisted, there is little opening area with respect to the line of magnetic force. Even when the electrode is used together with an apparatus such as MRI which produces a strong magnetic field, therefore, only a very low voltage is induced in the lead wires 12a to 12c, and hence little noises are produced.

As shown in FIG. 2, it is applicable for drawing the twisted lead wire from the vicinity of center portion of the electrode 10 like in shape of T-type.

Second Embodiment of the Electrode for Measuring a Biomedical Signal

Figure 3:
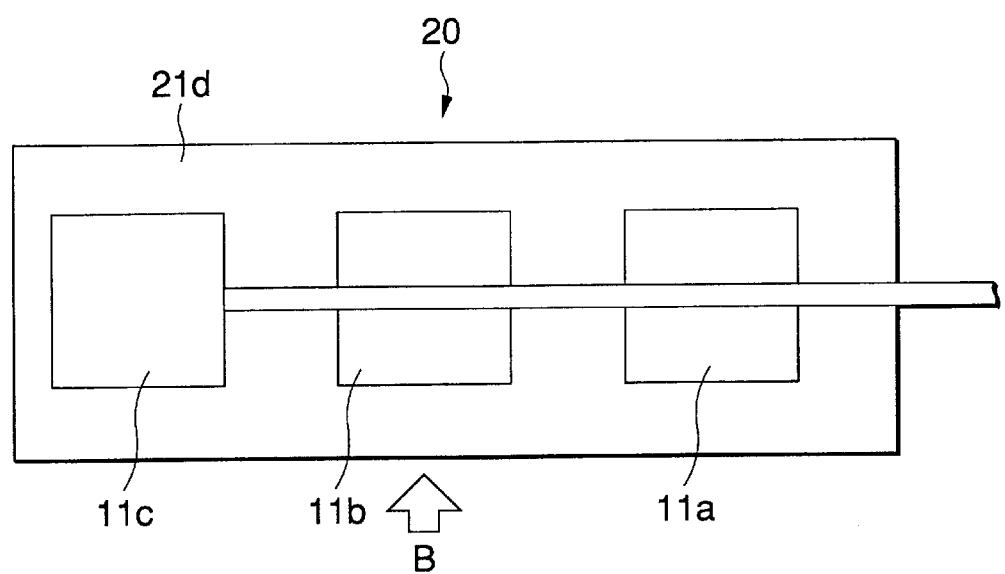
FIG. 3 is a plan view showing a second embodiment of the electrode for measuring a biomedical signal of the invention.
Figure 4:
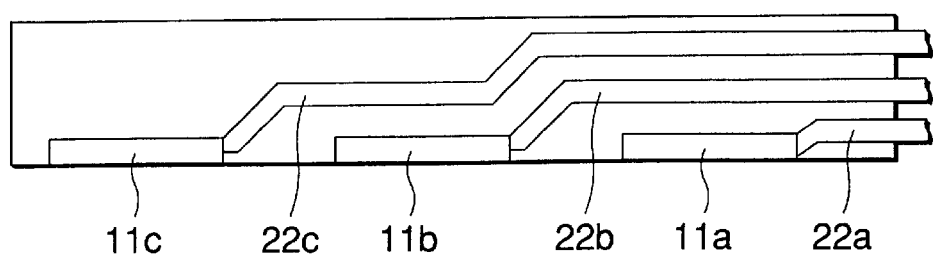
FIG. 4 is a section view taken along the line B—B of FIG. 3.

FIG. 3 is a perspective view from the upper side showing a second embodiment of the electrode for measuring a biomedical signal of the invention, and FIG. 4 is a section perspective view from the arrow B of FIG. 3.

In the embodiment, as shown in FIG. 3 and FIG. 4, the electrodes 11a to 11c are arranged with being staggered so as to be in a straight line and at constant intervals. Lead wires 22a to 22c are stacked so as to overlap one another in the thickness direction of the electrode body by molding with rubber or plastic, fixing the lead wires and minimizing the gap among the lead wires.

The disposition in which the lead wires 22a to 22c are stacked so as to overlap one another in the thickness direction of the electrode body can reduce the vertical opening area with respect to the line of magnetic force. The lateral opening area can be-reduced by forming the lead wires 22a to 22c so as to be thin.

As described above, in the electrode for measuring a biomedical signal 20 of second embodiment, the lead wires 22a to 22c are stacked so as to overlap one another in the thickness direction of the electrode body. In the lead wires 22a to 22c, therefore, the opening area in the thickness direction with respect to the line of magnetic force is reduced. As a result, even when the electrode is used together with an apparatus such as MRI which produces a strong magnetic field, only a very low voltage is generated in the lead wires 22a to 22c, and hence little noises are produced.

The electrodes 11a to 11c and the lead wires 22a to 22c may be formed by using flexible printing board, that reduces the lateral opening area and forms the electrode to be thin.

(III) Third Embodiment of the Electrode for Measuring a Biomedical Signal

Figure 5:
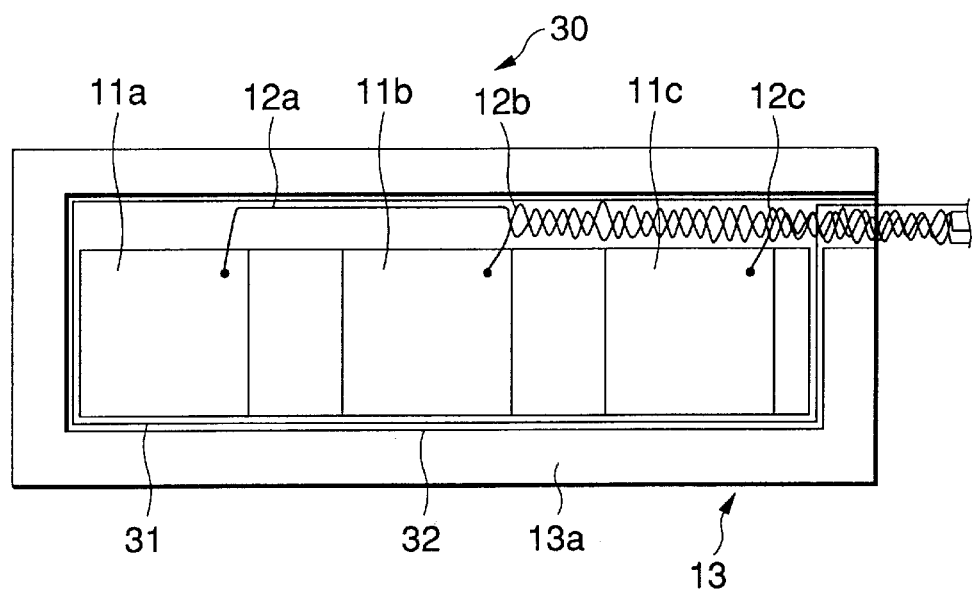
FIG. 5 is a plan view a third embodiment of the electrode for measuring a biomedical signal of the invention.

FIG. 5 is a perspective view from the upper side showing a third embodiment of the electrode for measuring a biomedical signal of the invention.

The electrode for measuring a biomedical signal 30 of the third embodiment comprises a noise-detecting sensor 31 which detects a current flowing through lead wires 12a to 12c placed in a strong magnetic field. The sensor 31 is configured by disposing a conductive wire in a support section 13, in a shape of a loop, and inserted into a groove 32 which is formed so as to surround electrodes 11a to 11c of a plate-like member 13a of the support section 13. Since the conductive wire is disposed in a loop so as to have an opening area with respect to the line of magnetic force, a voltage of the level which is sufficient for detecting noises is generated and noises can be surely detected.

Namely, the conductive wire is arranged in the vicinity of the electrode. It is preferable for definding the loop in such a manner the conductive wire surrounds at least one of the positive electrode and the negative electrode.

Figure 6:
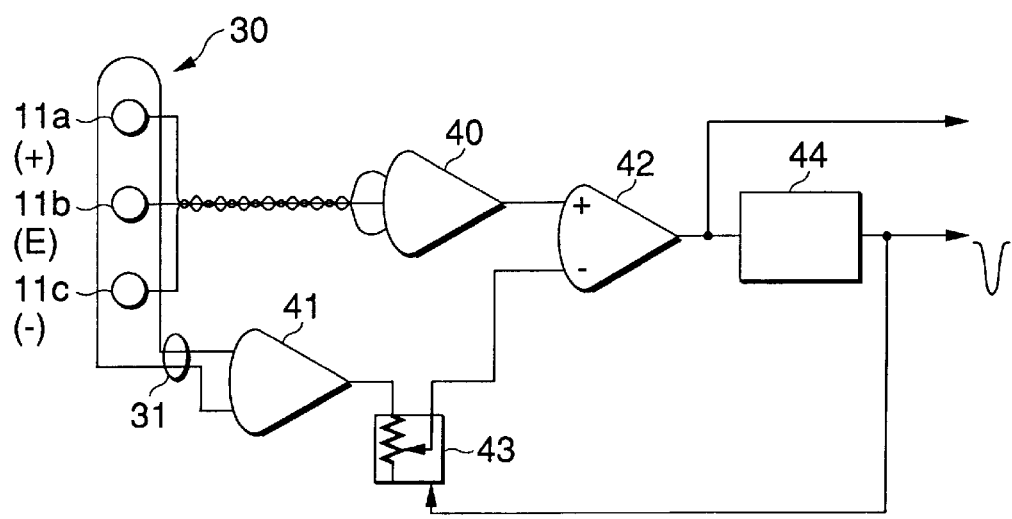
FIG. 6 is a block diagram showing the configuration of a signal processing circuit using the electrode for measuring a biomedical signal of third embodiment.

FIG. 6 is a block diagram showing the configuration of a signal processing circuit using the electrode for measuring a biomedical signal 30. Referring to the figure, a biomedical signal obtained in the electrodes 11a to 11c is amplified by an amplifier 40, and a signal obtained in the sensor 31 is amplified by an amplifier 41. An output of the amplifier 40 is supplied to a noninverting input of a comparator 42, and that of the amplifier 41 is supplied via an subtracter 43 to an inverting input of the comparator 42. The comparator 42 produces an output corresponding to a difference between the outputs of the amplifiers 40 and 41. The output is supplied to a measuring circuit which is not shown, and also to a noise detecting section 44. The noise detecting section 44 detects noise components from the output of the comparator 42, and adjusts the attenuation rate of the subtracter 43 so that the noise level becomes zero.

(IV) Embodiment of the Electrode Support Device for Measuring a Biomedical Signal.

Figure 7:
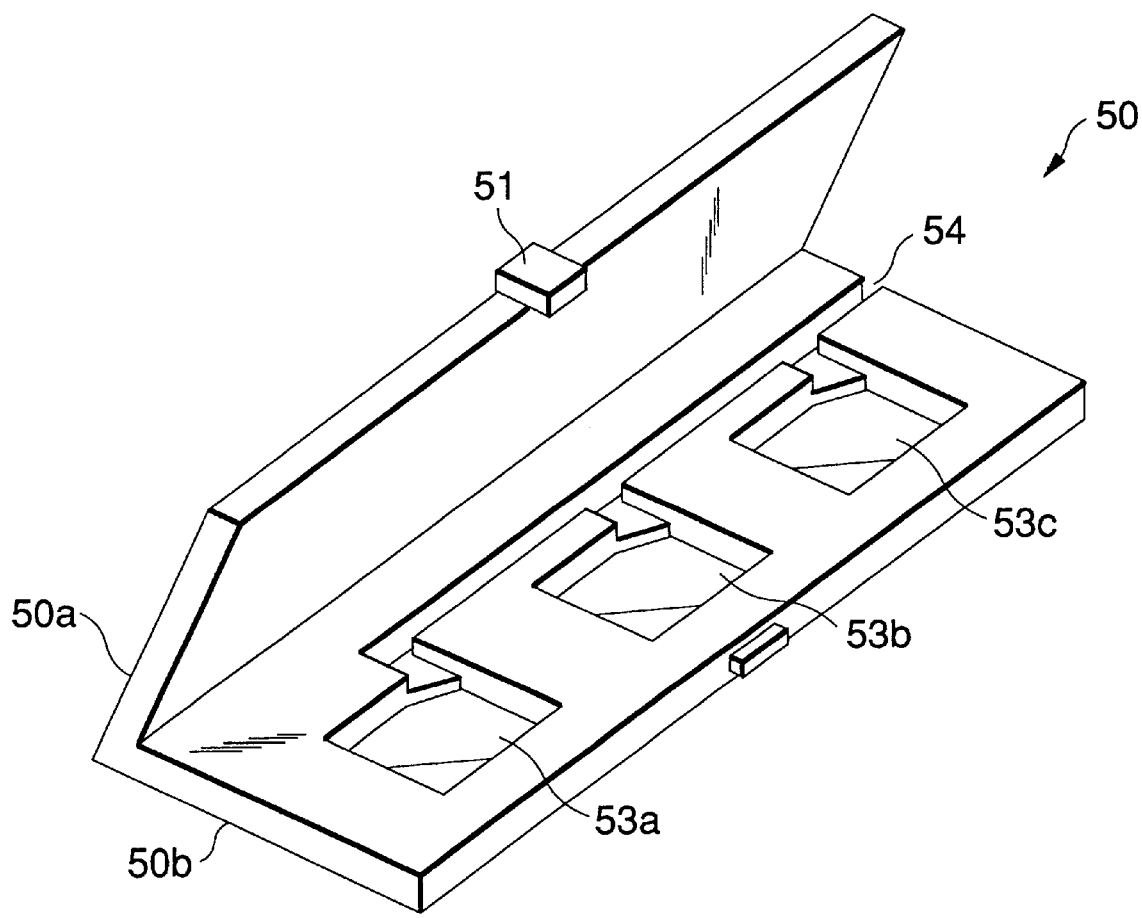
FIG. 7 is a perspective view showing an embodiment of the electrode support device for measuring a biomedical signal of the invention.
Figure 8:
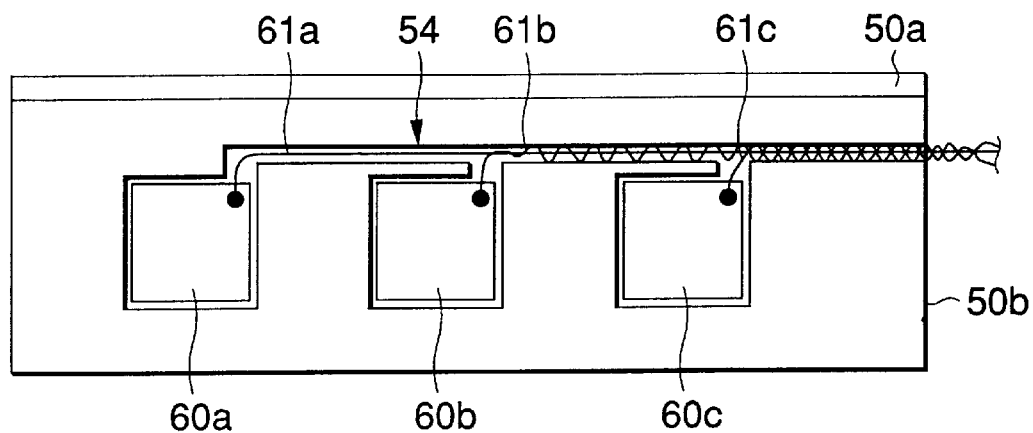
FIG. 8 is a plan view of a part of the embodiment of the electrode support device for measuring a biomedical signal.

FIG. 7 is a perspective view showing an embodiment of the electrode support device for measuring a biomedical signal of the invention, and FIG. 8 is a plan view showing a part of the tool.

The electrode support device for measuring a biomedical signal (hereinafter, referred to merely as "electrode support device") 50 of the embodiment is configured by two portions (hereinafter, referred to as "plate-like members") 50a and 50b which are made of a flexible material such as rubber or plastic and which are formed into a rectangular shape. In one of the plate-like members or the plate-like members 50b, housing portions 53a to 53c which respectively houses electrodes 60a to 60c (see FIG. 8) for taking out a biomedical signal, and a thin groove 54 which houses lead wires 61a to 61c respectively connected to the electrodes 60a to 60c are formed. The electrodes 60a to 60c are identical with those which are independently used in the prior art.

Figure 9:
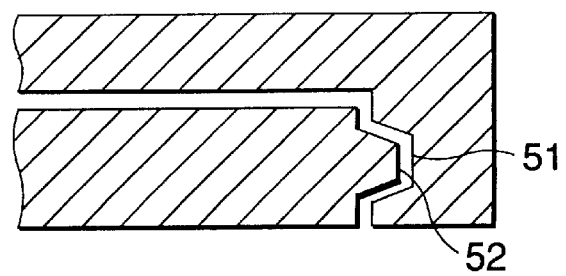
FIG. 9 is a section view of a part of the embodiment of the electrode support device for measuring a biomedical signal.
Figure 10:
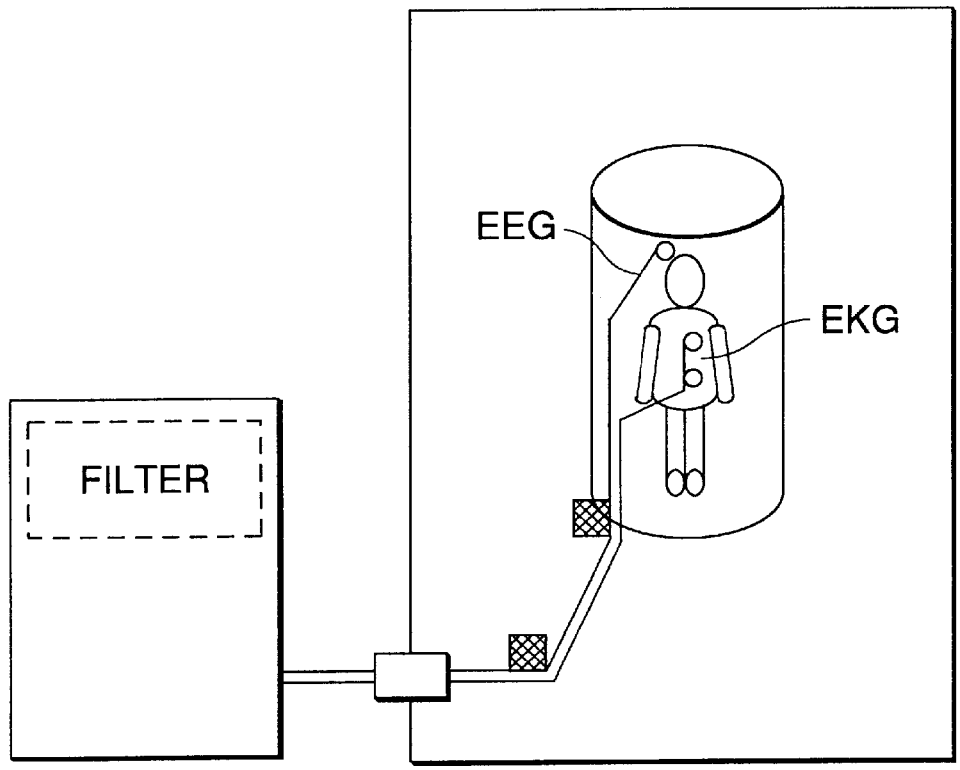
FIG. 10 is a view diagrammatically showing the configuration of MRI.
Figure 11:
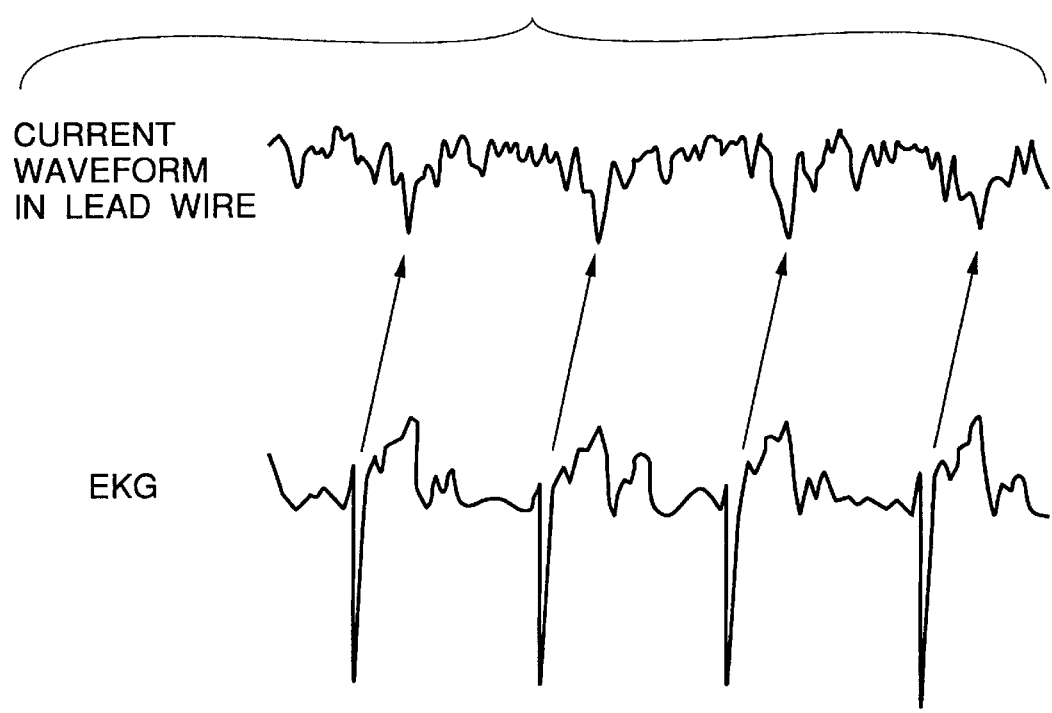
FIG. 11 is a waveform chart showing an electrocardiogram and a current generated in a lead wire.

As shown in the plan view of FIG. 8, the groove 54 is formed so as to elongate in the arrangement direction of the housing portions 53a to 53c and in adjacent to the housing portions 53a to 53c. As shown in the perspective view of FIG. 7, the plate-like members 50a and 50b are coupled together by means of a hinge between their edges elongating in their longitudinal direction, so as to be openable with respect to each other. Engaging pieces 51 and 52 are respectively formed at the middle portions of the opening edges of the plate-like members 50a and 50b, so that the plate-like members in the closing state are hardly opened. As shown in a section view of FIG. 9, a recess is formed in a middle portion of the inner side of the engaging piece 51, and the engaging piece 52 can be fitted into the recess. When the engaging piece 52 is fitted into the recess of the engaging piece 51 in this way, the plate-like members 50a and 50b can be surely closed.

When the thus configured electrode support device 50 is to be used, the plate-like members 50a and 50b are opened, and the electrodes 60a to 60c are placed into the housing portions 53a to 53c of the plate-like member 50b, respectively. Thereafter, the lead wires 61a to 61c are placed into the groove 54. At this time, the lead wires 61a to 61c are twisted. After the electrodes 60a to 60c and the lead wires 61a to 61c are inserted, the plate-like members 50a and 50b are closed.

In the configuration in which the lead wires 61a to 61c are housed in a compacted state, the lead wires 61a to 61c have little opening area with respect to the line of magnetic force. Even when the electrode support device is used together with an apparatus such as MRI which produces a strong magnetic field, therefore, only a very low voltage is generated in the lead wires 61a to 61c, and hence little noises are produced.

A groove which accommodates the noise-detecting sensor 31 may be disposed in the electrode support device 50.

The shape of the electrode support device is not restricted to that of the embodiment. The electrode support device may have any shape as far as the electrodes 60a to 60c can be housed and the lead wires 61a to 61c can be housed in a straight line.

According to the electrode for measuring a biomedical signal of the present invention, the lead wires respectively connected to the electrodes are tightly twisted so that the opening area with respect to the line of magnetic force is minimum. Even when the electrode is placed in a strong magnetic field such as MRI, little noises are produced. As a result, correct measurement results can be obtained in an electrocardiogram or an electroencephalogram.

According to the electrode for measuring a biomedical signal of the present invention, the lead wires respectively connected to the electrodes are stacked so as to overlap one another in the thickness direction of the electrode body so that the opening area with respect to the line of magnetic force is minimum. Even when the electrode is placed in a strong magnetic field such as MRI, little noises are produced. As a result, correct measurement results can be obtained in an electrocardiogram or an electroencephalogram.

According to the electrode for measuring a biomedical signal of the present invention, the sensor which detects a voltage corresponding to the number of crossing magnetic fluxes is disposed. When the electrode for measuring a biomedical signal is placed in a magnetic field, therefore, it is possible to pick up noises synchronized with an electrocardiogram. The picked-up noises can be used for canceling noises of a low level which are contained in a biomedical signal obtained from the electrode for measuring a biomedical signal.

According to the electrode support device for measuring a biomedical signal of the present invention, the lead wires respectively connected to the electrodes can be fixed in a straight line, and hence the opening area in the stack direction with respect to the line of magnetic force can be reduced. As a result, even when the electrode support device is used together with an apparatus such as MRI which produces a strong magnetic field, generation of noises due to a current flowing through each lead wire can be suppressed to a low level. Furthermore, the sensor which detects a voltage corresponding to the number of crossing magnetic fluxes is disposed. When the electrode support device for measuring a biomedical signal is placed in a magnetic field, therefore, it is possible to pick up noises synchronized with an electrocardiogram. The picked-up noises can be used for canceling noises of a low level which are contained in a biomedical signal obtained from an electrode for measuring a biomedical signal.

What is claimed is:

1. An electrode for measuring a biomedical signal comprising:
   a plurality of electrodes for taking out a biomedical signal;
   lead wires respectively connected to said electrodes; and
   a support member for supporting and insulating said plurality of electrodes therein, said support member made of a flexible and insulative material, wherein a portion of said lead wires disposed in said support member is tightly twisted and disposed in a straight line for suppressing noise from being generated therein.

2. An electrode for measuring a biomedical signal comprising:
   a plurality of electrodes for taking out a biomedical signals
   lead wires respectively connected to said electrodes;
   a support member for supporting and insulate said plurality of electrodes and said lead wires, said support member made of a flexible and insulative material, said lead wires tightly twisted in said support member and said twisted lead wires disposed in a straight line; and
   a sensor supported by said support member, said sensor generating a current corresponding to the number of crossing magnetic fluxes when said sensor is placed in a magnetic field.

3. The electrode for measuring a biomedical signal according to claim 2, wherein said sensor is defined by disposing a conductive wire in said support member in a shape of a loop.

4. The electrode for measuring a biomedical signal according to claim 3, wherein said sensor is defined by disposing a conductive wire so as to surround at least one of the plurality of electrodes in a shape of a loop.

5. The electrode for measuring a biomedical signal according to claim 1, wherein said twisted lead wires are drawn from the vicinity of a center portion of said electrode.

6. An electrode support device for measuring a biomedical signal comprising:

a plurality of housing portions, made of flexible and insulative material, for accommodating a plurality of electrodes for taking out a biomedical signal; and a groove formed in said support device through which all lead wires respectively connected to said plurality of electrodes are drawn out in a single straight line to an outside, said groove formed for accommodating said lead wires from a point where said lead wires exit from said plurality of housing portions to said outside, such that open space is minimized between lead wires respectively connected to said plurality of electrodes.

7. The electrode support device for measuring a biomedical signal according to claim 5, further comprising:

an accommodating portion formed in said support device accommodating a sensor, said sensor generating a current corresponding to the number of crossing magnetic fluxes when said sensor is placed in magnetic field.

8. An apparatus for measuring a biomedical signal comprising:

a plurality of electrodes for taking out a biomedical signal;

a plurality of lead wires connecting the electrodes, respectively;

a support member for supporting and insulating said electrodes and said lead wires, said support member made of a flexible and insulative material, said plurality of lead wires grouped together such that they exit said support member in a single line for minimizing open space between said plurality of lead wires;

a sensor disposed in said support member for generating a current corresponding to the number of crossing magnetic fluxes sensor when said sensor is placed in a magnetic field, said sensor outputting a signal indicative of said magnetic fluxes;

a comparator electrically connected to said sensor and said plurality of lead wires, said comparator calculating a difference between outputs of said electrodes and said sensor, said comparator outputting a compared signal;

a noise detector electrically connected to said comparator for detecting noises due to the magnetic fluxes based on said compared signal output from said comparator, said noise detector outputting a detected noise signal; and an attenuator electrically connected to said sensor, to said comparator, and to said noise detector, said attenuator adjusting the output of said sensor so as to minimize the output of said noise detector, therein said attenuator is adjusted according to the output of said noise detector.

9. The apparatus for measuring a biomedical signal according to claim 8, wherein said sensor is defined by disposing a conductive wire in said support in a shape of a loop.

10. The apparatus for measuring a biomedical signal according to claim 9, wherein said sensor is defined by disposing a conductive wire so as to surround at least one of the plurality of electrodes in a shape of a loop.

11. An electrode for measuring a biomedical signal comprising:

a plurality of electrodes for taking out a biomedical signal;

lead wires respectively connected to said electrodes; and a plate-like shaped support member for supporting and insulating said plurality of electrodes and said lead wires, said support member having a width and a thickness perpendicular to said width, and made of a flexible and insulative material, wherein said plurality of electrodes is disposed so as to avoid overlapping one another and wherein said lead wires are stacked so as to overlap one another in a thickness direction of the electrode in a contactless manner.

* * * * *